United States Patent [19]

Knöfel et al.

[11] 4,087,459

[45] May 2, 1978

[54] PROCESS FOR THE PREPARATION OF POLYAMINES

[75] Inventors: Hartmut Knöfel, Leverkusen; Gunther Ellendt, Krefeld, both of Germany

[73] Assignee: Bayer Aktiengesellschaft, Leverkusen, Germany

[21] Appl. No.: 696,662

[22] Filed: Jun. 16, 1976

[30] Foreign Application Priority Data

Jun. 27, 1975 Germany .............................. 2528694

[51] Int. Cl.² .............................................. C07C 85/24
[52] U.S. Cl. ................................................. 260/570 D
[58] Field of Search .................................... 260/570 D

[56] References Cited

U.S. PATENT DOCUMENTS

| B 518,076 | 3/1976 | Piston et al. | 260/570 X |
|---|---|---|---|
| 3,478,099 | 11/1969 | Ross et al. | 260/570 |
| 3,542,871 | 11/1970 | Thompson | 260/570 |
| 3,952,042 | 4/1976 | Knofel | 260/453 |

FOREIGN PATENT DOCUMENTS

| 2,343,638 | 3/1975 | Germany | 260/570 |

*Primary Examiner*—Robert V. Hines
*Attorney, Agent, or Firm*—Gene Harsh; Joseph C. Gil

[57] ABSTRACT

The instant invention is directed to a process for the preparation of multinuclear aromatic polyamines by the condensation of aniline with formaldehyde in the presence of water and acid catalysts, in which the completely reacted aqueous condensation mixture is extracted with a hydrophobic solvent in extraction stage (I), optionally with the addition of aniline, the resulting solvent phase is worked-up in known manner to isolate the polyamine and the aqueous phase is recycled to the beginning of the process, the improvement characterised in that before the aqueous phase is returned to the beginning of the process, it is extracted in one or more separate extractors (II) with a hydrophobic solvent which may contain aniline and/or aniline/formaldehyde condensates with an increased proportion of ortho-isomers, the resulting solvent phase or phases is or are extracted with the aqueous acid condensation mixture in one or more separate extractors (III) at any one or more points after the first condensation stage and before the main extraction stage (I), and the resulting solvent phase or phases is or are returned to extractor or extractors (II).

15 Claims, 7 Drawing Figures

PROCESS FOR THE PREPARATION OF POLYAMINES

BACKGROUND OF THE INVENTION

In U.S. Application No. 383,921, filed on July 30, 1973 and now U.S. Pat. No. 3,996,283, there has been described a process for the preparation of multinuclear aromatic polyamines by the condensation of aniline with formaldehyde in the presence of water and acid catalysts, wherein the reacted aqueous condensation mixture is extracted with a hydrophobic solvent, optionally with the addition of a further quantity of aniline. The resulting solvent phase is worked-up in known manner to isolate the polyamine, and the aqueous phase is recycled to the beginning of the process after the addition of fresh aniline. The processes described in U.S. Pat. 3,952,042 for the preparation of aniline/formaldehyde condensates are improved or particular embodiments of the process described in the above-identified U.S. Application.

DESCRIPTION OF THE INVENTION

The present invention has as one of its objects a process for the preparation of multinuclear aromatic polyamines by the condensation of aniline with formaldehyde in the presence of water and acid catalysts, in which the reacted aqueous condensation mixture is extracted with a hydrophobic solvent in one extraction stage (I), optionally with the addition of aniline, and the resulting solvent phase is worked-up in known manner to isolate the polyamine while the aqueous phase is recycled to the beginning of the process, characterised in that before the aqueous phase is returned to the beginning of the process, it is extracted in one or more separate extractors (II) with a hydrophobic solvent which may contain aniline and/or aniline/formaldehyde condensates with an increased proportion of ortho-isomers, the resulting solvent phase or solvent phases is or are in turn extracted with the aqueous, acid condensation mixture in one or more separate extractors (III) situated at any point or points after the first condensation stage and before the main extraction stage (I), and the solvent phase or phases thereby obtained is or are returned to the extractor or extractors (II).

The individual possible embodiments of the process according to the present invention will now be described in more detail with reference to FIGS. 1 through 7 of the accompanying drawings in which the reference numerals have the following meanings:

(1) a tank for aniline,
(2) a tank for aqueous formalin solution,
(3) the first condensation reactor,
(4) the last condensation reactor,
(5) the main extraction stage (I),
(6) extraction stage (II) consisting of one or more single stage or multistage (6a and 6b) extractors,
(7) extractor stage (III) consisting of one or more single stage or multistage (7a and 7b) extractors,
(8) the single stage or multistage (8a and 8b) distillation plant.
(9) a tank for effluent water,
(10) a tank for the product of the process and
(11) an additional extraction stage.

For the sake of simplification, the invention will be described for the production of aromatic polyamine from aniline and formaldehyde.

Figure 1:
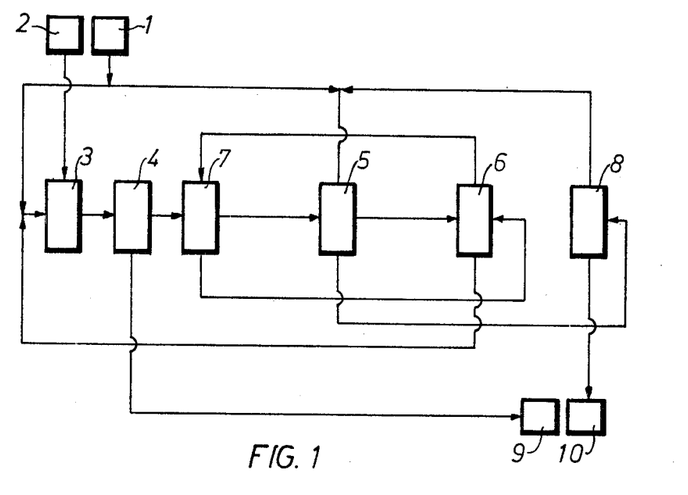
FIGS. 1 through 7 schematically set forth various embodiments of the instant invention.

The first embodiment of the process according to the present invention (see FIG. 1) constitutes a major improvement to the process described in U.S. Pat. No. 3,952,042 for the preparation of polyamines having a low proportion of orthoisomers. Thus, for example, in the earlier process, it is possible to operate with a degree of protonation of almost 100% (degree of protonation = percentage of amine nitrogen atoms present in the form of ammonium ions, based on the total quantity of amine nitrogen atoms present) in order to obtain polyamines having a very low proportion of orthoisomers. Since, on the other hand, extraction of the product of the process from the aqueous phase by means of a hydrophobic solvent cannot be carried out at a degree of protonation of 100% without the addition of aniline before extraction, it is necessary, in order to re-establish the high degree of protonation in the aqueous phase, to remove the free amine still present in the aqueous phase after the main extraction by washing the aqueous phase, preferably with a solvent which is free from amine. In the earlier process, in order to recover the solvent used for this washing operation, the organic phase leaving the washing operation must be separated into its constituents by distillation. In the first embodiment of the process according to the present invention, this step of distillation may now be avoided since the mixture of solvent and amine leaving this final washing operation is extracted together with the aqueous phase after the last condensation stage and before the main extraction stage. This at the same time has the desired effect of increasing the concentration of free amine in the aqueous condensation mixture as required for extraction of the product of the process in the main extraction stage. In this first embodiment of the process according to the present invention, the extraction conditions [indices of the extractors (6) and (7), and temperature employed for extraction] are preferably selected so that the hydrophobic solvent leaving extractor (7) (extraction stage (III)) is practically free from aniline and the aqueous phase which leaves extractor (6) (extraction stage (III)) and is returned to the beginning of the process has a degree of protonation of from 90 to 100%. More particularly, the first embodiment comprises the steps of:

(A) condensing an aromatic amine with formaldehyde in the presence of an aqueous acid catalyst to obtain the condensation mixture as a first aqueous phase containing said aromatic polyamines, (B) extracting a first solvent phase with said first aqueous phase to provide a second solvent phase and a second aqueous phase containing said aromatic polyamines, (C) extracting said second aqueous phase with a hydrophobic solvent to provide a third solvent phase and a third aqueous phase containing the acid catalyst as an amine salt of said aromatic amine and of said aromatic polyamine, (D) recovering said aromatic polyamines from said third solvent phase, (E) extracting said third aqueous phase with said second solvent phase to provide said first solvent phase and a fourth aqueous phase containing the acid catalyst and amine salt of said aromatic amines and of said aromatic polyamines, (F) returning said first solvent phase to step (B), and
(G) returning said fourth aqueous phase to step (A).

Figure 2:
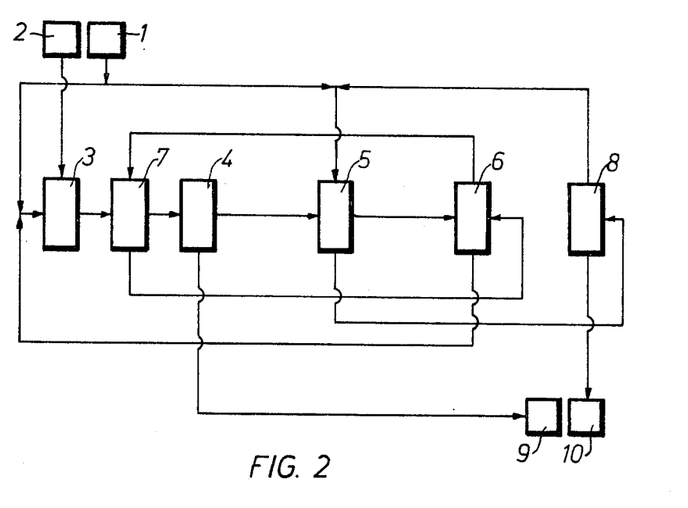

The second embodiment (see FIG. 2) of the process according to the present invention differs from the first embodiment solely by the fact that extractor (7) (extraction stage (III)) is arranged before the last condensation stage, but after the first condensation stage. As a result of this arrangement, the aqueous condensation mixture has an increased aniline content (higher aniline/formaldehyde ratio) even before termination of the condensation reaction, thereby enabling polyamines having an increased content of dinuclear condensation products to be prepared while at the same time reducing the proportion of o-isomers in the products of the process. More particularly, the second embodiment comprises the steps of:

(A) pre-condensing an aromatic amine with formaldehyde in the presence of an aqueous acid catalyst in a first condensation stage to obtain a precondensation mixture as a first aqueous phase, (B) extracting a first solvent phase with said first aqueous phase to provide a second solvent phase and a second aqueous phase, (C) subjecting said second aqueous phase to a final condensation reaction to obtain a condensation mixture as a third aqueous phase containing said aromatic polyamines, (D) extracting said third aqueous phase with a hydrophobic solvent to provide a third solvent phase and a fourth aqueous phase containing the acid catalyst as an amine salt of said aromatic amine and of said aromatic polyamines, (E) recovering said aromatic polyamines from said third solvent phase, (F) extracting said fourth aqueous phase with said second solvent phase to provide said first solvent phase and a fifth aqueous phase containing the acid catalyst as amine salt of said aromatic amine and of said aromatic polyamines, (G) returning said first solvent phase to step (B), and (H) returning said fifth aqueous phase to step (A).

Figure 3:
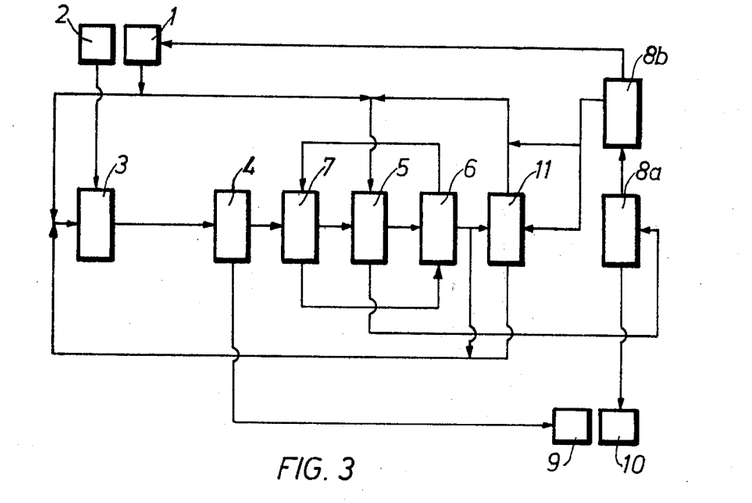

The third embodiment (see FIG. 3) of the process according to the present invention is identical to the first embodiment in its arrangement of extractors (6) and (7). It differs from the first embodiment, in particular, by the fact that the proportions of the individual components [aniline/solvent ratio of the stream of solvent cycling through (6) and (7)] and the conditions under which extraction is carried out are selected so that the solvent phase leaving extractor (7) (extraction stage (III)) still contains free aniline in addition to solvent, and in particular, also the major proportion of 2,2'- and 2,4'-diaminodiphenylmethane of the aqueous phase leaving reactor (4) (these ortho-isomers are preferentially extracted compared with 4,4'-diaminodiphenylmethane). In extractor (6) (extraction stage (II)) these ortho-isomers are then taken up again by the aqueous phase which is to be returned to the beginning of the process. Since, on the other hand, the ortho-isomers preferentially continue to react with formaldehyde to form higher nuclear condensation products, a polyamine mixture is obtained which contains a particularly low proportion of 2,2'- and 2,4'-diaminodiphenylmethane. Owing to the higher proportion of aniline contained in the solvent phase circulating through (6) and (7) compared with the aniline content in this solvent phase in embodiments 1 and 2, the aqueous phase leaving extractor (6) also always contains free amine so that in order to re-establish a high degree of protonation it may be advisable to wash the aqueous phase leaving extractor (6) with pure solvent in an extractor (11) before it is returned to the beginning of the process. In this washing operation in extractor (11), aniline is preferably removed from the aqueous phase in the form of the free base. The aniline-containing solvent leaving extractor (11) may be directly returned to the main extractor (5) (extraction stage (I)), if desired after further addition of aniline. This optional washing operation in extraction (11) with pure solvent, however, requires an additional distillation operation since the solvent phase leaving the main extraction stage (5) must then be separated by distillation into the product of the process, aniline and pure solvent whereas if the final washing (11) is omitted, it is not necessary to separate the excess aniline from the solvent, in fact in such a case distillation of the organic phase leaving the main extractor (5) to separate it into its components may consist simply of distilling off the mixture of aniline and solvent from the product of the process. This mixture may then, as in embodiments 1 and 2, be returned directly to the main extractor (5) optionally after further addition of aniline. Even if the final washing (11) is omitted, the products obtained in the third embodiment of the process according to the present invention are distinguished by a low 2,2'- and 2,4'-diaminodiphenylmethane content although omission of the final washing has the effect that at the beginning of the condensation reaction the degree of protonation is below 90%. The increased proportions of 2,2'- and 2,4'-isomers formed as aresult of this reduced degree of protonation will in the extreme case be completely returned to the beginning of the process and then continue to react to form higher nuclear condensation products. The third embodiment accordingly is similar to the first embodiment wherein step (E) comprises:

(E i) extracting said third aqueous phase with said second solvent phase to provide said first solvent phase, and a fifth aqueous phase containing the acid catalyst as an amine salt of said aromatic amine and of said aromatic polyamines, and (E ii) extracting said fifth aqueous phase with a hydrophobic solvent to provide a fourth solvent phase and said fourth aqueous phase containing the acid catalyst as an amine salt of said aromatic amine and of said aromatic polyamines.

Figure 4:
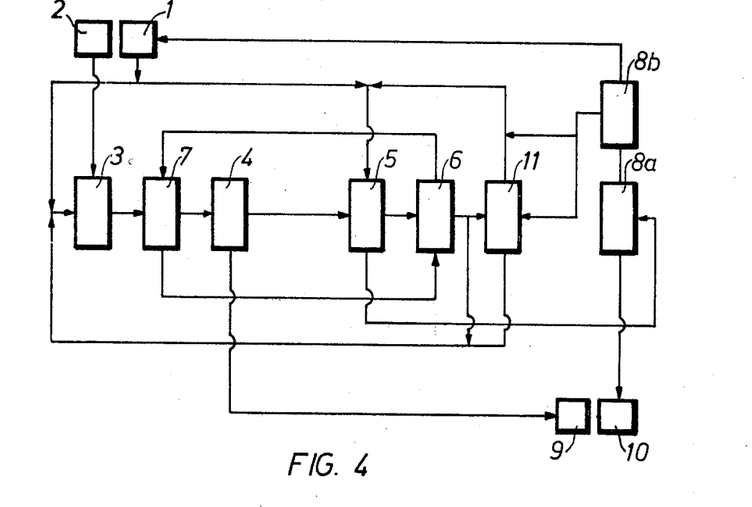

The fourth embodiment of the process according to the present invention (see FIG. 4) is substantially similar to the third embodiment with this one difference that the extractor (7) (extraction stage (III)) is arranged behind the first and in front of the last condensation stage. It is thereby possible to achieve the effect that the solvent phase leaving extractor (7) contains the bulk of the N-(2-aminobenzyl)-aniline present in the aqueous phase leaving reactor (3). N-(2-aminobenzyl)-aniline is preferentially extracted from the aqueous phase compared with p-aminobenzylaniline. If the organic phase leaving extractor (7) is reextracted in extractor (6) with the aqueous phase leaving extractor (5), o-aminobenzylaniline is returned to the aqueous phase and from there it is returned to the beginning of the process, optionally after first being washed in extractor (11). Since N-(2-aminobenzyl)-aniline continues to react with formaldehyde in preference to aniline, the formation of secondary products from o-aminobenzylaniline is in this way suppressed. One particularly desirable effect of this is that the product finally obtained from the process is practically free from 2,2'-diaminodiphenylmethane since this diamine may be formed solely via the intermediate stage of N-(2-aminobenzyl)-aniline. In this fourth embodiment, aniline may again be removed from the aqueous phase by washing with pure solvent in the optional washing stage in extractor (11) in order to increase the degree of protonation in the aqueous phase, but the resulting complications indicated in the description of the third embodiment again apply. The fourth embodiment is thus similar to the second embodiment wherein step (F) comprises:

(F i) extracting said fourth aqueous phase with said second solvent phase to provide said first solvent phase and a sixth aqueous phase containing the acid catalyst as an amine salt of said aromatic amine and of said aromatic polyamines, and (Fii) extracting the sixth aqueous phase with a hydrophobic solvent to provide a fourth solvent phase and said fifth aqueous phase containing the acid catalyst as amine salt of said aromatic amine and of said aromatic polyamines.

Figure 5:
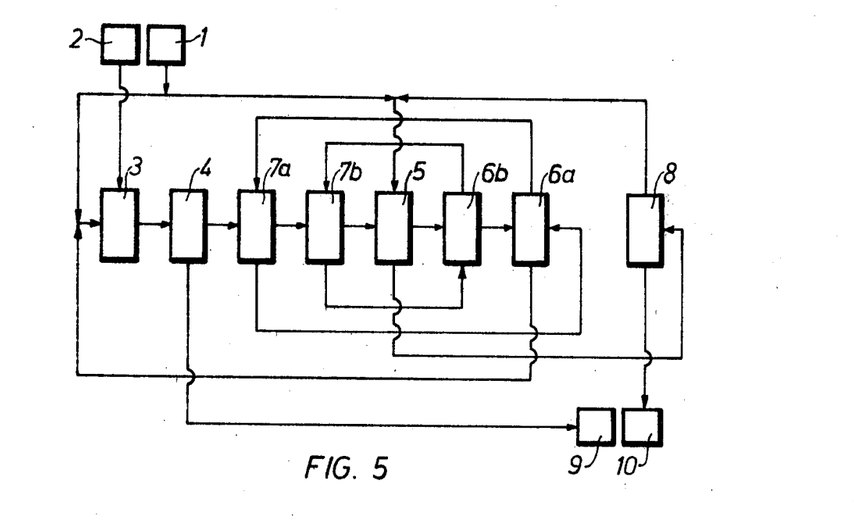

The fifth embodiment of the process according to the present invention (see FIG. 5) constitutes a combination of the first and third embodiment. In this case, extraction stage (II) consists of two extractors (6a) and (6b) connected in series and extraction stage (III) consists of two extractors (7a) and (7b) connected in series. The outer circulation of solvent through (6a) and (7a) serves, as in the first embodiment, to increase the degree of protonation in the aqueous phase returned to the beginning of the process and at the same time to increase the concentration of free aniline in the aqueous phase leaving the last reactor (4). The composition of the solvent phase leaving extractor (7a) is similar to the composition of the solvent phase leaving extractor (7) in the first embodiment. The inner circulation of solvent through (6b) and (7b) corresponds to the circulation of solvent through (6) and (7) in the third embodiment and serves to further increase the concentration of aniline in the aqueous phase before the main extraction (5) and at the same time to remove aniline from the aqueous phase after the main extraction (5). Side-by-side with this, ortho-isomers are returned to the beginning of the process by way of the inner solvent circulation through (6b) and (7b). The fifth embodiment of the process according to the present invention is therefore particularly suitable for the preparation of products having a greatly reduced proportion of o-isomers. The fifth embodiment is thus similar to the first embodiment wherein step (B) comprises:

(B i) extracting said first solvent phase with said first aqueous phase to provide said second solvent phase and a sixth aqueous phase containing said aromatic polyamines, and (Bii) extracting a fourth solvent phase with said sixth aqueous phase to provide a fifth solvent phase and said second aqueous phase containing said aromatic polyamines, and wherein step (E) comprises:

(E i) extracting said third aqueous phase with said fifth solvent phase to provide said fourth solvent phase and a seventh aqueous phase containing the acid catalyst as an amine salt of said aromatic amine and of said aromatic polyamines, (Eii) returning said fourth solvent phase to step (Bii), and (Eiii) extracting said seventh aqueous phase with said second solvent phase to provide said first solvent phase and said fourth aqueous phase containing the acid catalyst an an amine salt of said aromatic amine and of said aromatic polyamines.

Figure 6:
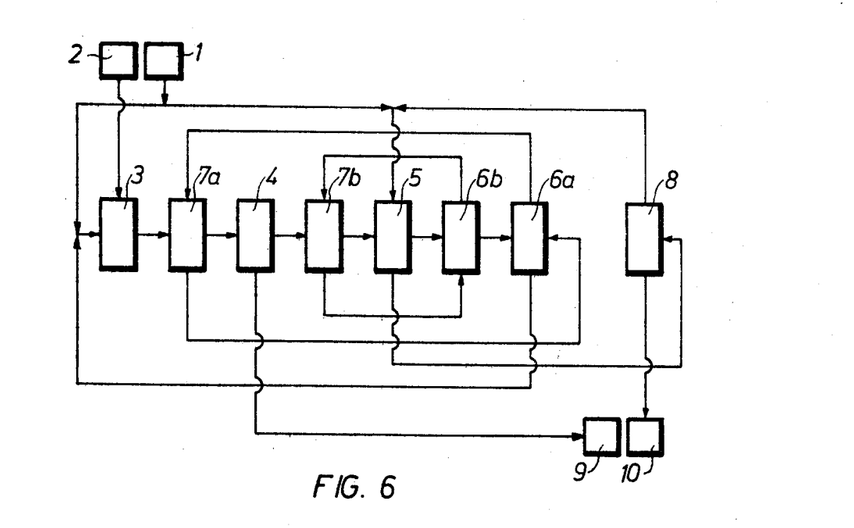

The sixth embodiment of the process according to the present invention (see FIG. 6) constitutes a combination of the second and third embodiment. It thus differs from the fifth embodiment by the fact that extractor (7a) of extraction stage (III) is arranged in front of the last condensation stage (4). The outer circulation of solvent through (6a) and (7a) increases the concentration of free aniline in the aqueous condensation mixture before the mixture enters the last condensation stage, thereby enabling polyamines having an increased content of higher nuclear homologues to be prepared. The composition of the solvent phase leaving extractor (7a) is similar to that of the solvent phase leaving extractor (7) in embodiment 2. Ortho-isomers are again returned to the beginning of the process through the inner circulation via (6b) and (7b), by-passing the main extraction stage (I). More particularly, the embodiment comprises the steps:

(A) precondensing an aromatic amine with formaldehyde in the presence of an aqueous acid catalyst in a first condensation stage to obtain a precondensation mixture as a first aqueous phase, (B) extracting a first solvent phase with said first aqueous phase to provide a second solvent phase and a second aqueous phase, (C) subjecting said second aqueous phase to a final condensation reaction to obtain a condensation mixture as a third aqueous phase containing said aromatic polyamines, (D) extracting a third solvent phase with said third aqueous phase to provide a fourth solvent phase and a fourth aqueous phase containing aromatic polyamines, (E) extracting said fourth aqueous with a hydrophobic solvent to provide a fifth solvent phase and a fifth aqueous phase containing the acid catalyst as an amine salt of said aromatic amine and of said aromatic polyamines, (F) recovering said aromatic polyamines from said fifth solvent phase.

(G) extracting said fifth aqueous phase with said fourth solvent phase to provide said third solvent phase and a sixth aqueous phase containing the acid catalyst as an amine salt of said aromatic amine and of said aromatic polyamines, (H) returning said third solvent phase to step (D), (I) extracting said sixth aqueous phase with said second solvent phase to provide said first solvent phase and a seventh aqueous phase containing the acid catalyst as an amine salt of said aromatic amine and of said aromatic polyamines, (J) returning said first solvent phase to step (B), and (K) returning said seventh aqueous phase to step (A).

Figure 7:
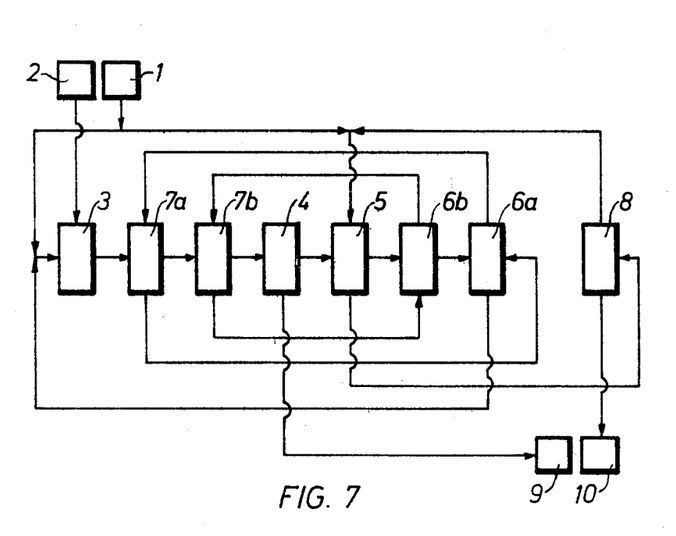

The seventh embodiment of the process according to the present invention (see FIG. 7) is a combination of embodiments 2 and 4. In this case, both extractors (7a) and (7b) of extraction stage (III) are arranged in front of the last condensation reactor (4), thereby enabling N-(2-aminobenzyl)-aniline to be preferentially returned to the beginning of the process, by-passing the main extraction stage (I), and at the same time ensuring a high degree of protonation in the aqueous phase leaving extractor (6a) and an increase in the concentration of aniline in the aqueous condensation mixture in extractor (7a), i.e. in front of the last condensation stage, so that the seventh embodiment of the process according to the present invention, in particular provides the possibility of preparing polyamines having an increased proportion of higher nuclear polyamines and at the same time a greatly reduced proportion of 2,2'-diaminodiphenylmethane. This embodiment is similar to the second embodiment wherein step (B) comprises:

(B i) extracting said first solvent phase with said first aqueous phase to provide said second solvent phase and a seventh aqueous phase, and (B ii) extracting a fourth solvent phase with said seventh aqueous phase to provide a fifth solvent phase and said second aqueous phase, and wherein step (F) comprises:

(F i) extracting said fourth aqueous phase with said fifth solvent phase to provide said fourth solvent phase and a eighth aqueous phase containing the acid catalyst as an amine salt of said aromatic amine and of said aromatic polyamines, (F ii) returning said fourth solvent phase to step (B ii), and (F iii) extracting said eighth aqueous phase with said second solvent phase to provide said first solvent phase and said fifth aqueous phase containing the acid catalyst as an amine salt of said aromatic amine and of said aromatic polyamines.

In the fifth, sixth and seventh embodiments of the process accordingly to the present invention, distillation stage (8) preferably merely effects a separation of the solvent phase leaving the main extractor (5) into the product of the process and a mixture of aniline and solvent which, as described in connection with the third embodiment, is used for extraction in extractor (5), if necessary after a further addition of aniline.

In all the embodiments of the process according to the present invention, the volumetric ratio of solvent phase to aqueous phase in extraction stages (II) and (III) is from 10:1 to 1:5 and preferably from 3:1 and 1:2. In the first and second embodiment of the process according to the present invention and in the circulations through (6a) and (7a) in embodiments 5, 6 and 7, the total amine content of the solvent leaving extraction stage (III) is generally from 0 to 15 volume percent and preferably from 0 to 10 volume percent. The total amine content in the solvent phase leaving extraction stage (III) in embodiments 3 and 4 and in the circulations through (6b) and (7b) in embodiments 5, 6 and 7 is generally from 15 to 70 volume percent and preferably from 15 to 30 volume percent. This amine content in the solvent phase leaving extraction stage (III) is a function of the aniline concentration in the total system and the efficiency of the extractors (6), (7), (6a), (7a), (6b) and (7b). Thus for example, a continuous transition from embodiment 1 to embodiment 3 or from embodiment 2 to embodiment 4 could be achieved while keeping the proportions of all the other components constant and the operating conditions of the system constant, simply by introducing more aniline into the system at one point than is continuously used by the aniline/formaldehyde condensation reaction. When making the transition from the first embodiment to the third embodiment or from the second embodiment to the fourth embodiment of the process according to the present invention, the increased addition of aniline could simply be continued until the solvent phase leaving extraction stage (III) has the desired total amine content. Transition from the first embodiment to the third embodiment or from the second to the fourth embodiment may also be achieved without altering the aniline concentration in the total system, simply by reducing the efficiency of extractor (6), for example, by increasing the extraction temperature or reducing the number of stages of extraction stage (6). This would have the result that the aqueous phase leaving (6) would have a higher aniline content than in embodiments (1) and (3), so that the aniline content in the aqueous phase entering at (7) would also be higher than in the first or third embodiment, with the result that the solvent phase leaving extractor (7) would be enriched not only in aniline, but as explained above, also in other bases. In one preferred variation of the third and fourth embodiments, free aniline (from container 1) is added to the aqueous phase before its entry into extractor (7) in order to ensure the desired high amine content in the solvent phase leaving extractor (7). This variation is particularly recommended when carrying out embodiments 3 and 4 of the process according to the present invention including the re-washing stage in extractor (11). The concentric circulations in embodiments 5, 6 and 7 differ mainly by their differing amine contents in the solvent phase leaving extractors (7a) and (7b). These differing amine contents in the concentric solvent circulations may be achieved and maintained by, for example, making extraction in extractors (6a) and (6b) less efficient (for example by employing higher temperatures and/or a smaller number of stages in the extractors) than in extractors (7a) and (7b).

The explanation so far given of the various embodiments of the process according to the present invention has been restricted to an explanation of those differences which essentially distinguish the process according to the present invention from the process according to U.S. Ser. No. 383,921 and U.S. Pat. No. 3,952,042. Common to all the embodiments of the process according to the present invention is the known principle of carrying out aniline/formaldehyde condensation, optionally in several stages, in the presence of acid, aqueous catalysts (in principle, the condensation in the process according to the present invention may be carried in more than two stages or, in the case of embodiments 1, 3 and 5, it may be carried out in a single stage), extraction of the resulting aqueous condensation mixture with a hydrophobic solvent in the main extraction stage (I) which is optionally multistage (indicated by the reference numeral (5) in all the figures), working-up of the resulting solvent phase by distillation in a single stage or multistage distillation column (8) or (8a) and (8b) and return of the aqueous phase leaving the main extraction stage to the beginning of the process via extraction stage (II).

Instead of using aniline, the process according to the present invention may in principle be carried out with any other aromatic amine, e.g., o-toluidine, m-toluidine, N-methylaniline, N-ethylaniline, 2,6-dimethylaniline, 2,6-diethylaniline, 2,6-diisopropylaniline or 2,4-diaminotoulene. Anthranilic acid alkyl esters containing from 1 to 4 carbon atoms in the alkyl group would also be suitable. These amines used in the process according to the present invention would result in amine/formaldehyde condensates completely analogous to the aniline/formaldehyde condensates.

Water-soluble acids suitable for the process according to the present invention are in particular those having a pKA-value below 2.5 and preferably below 1.5, for example hydrochloric acid, hydrobromic acid, sulphuric acid, trifluoroacetic acid, methanesulphonic acid, trifluoromethanesulphonic acid, benzene sulphinic acid or phosphoric acid. The preferred catalyst is hydrochloric acid. The acids mentioned above may also be used as mixtures with acid or neutral salts of such acids, for example, the corresponding ammonium or alkali metal salts. In the process according to the present invention, the said acids exist in the aqueous system in the form of the amine salts of the bases carried in the aqueous circulation.

The hydrophobic solvents used in the process according to the present invention may be any solvents having a boiling point approximately within the range of from 30° to 250° C and preferably from 80° to 200° C which are immiscible with water and inert towards the reactants. Examples of particularly suitable solvents of this type include chlorobenzene, dichlorobenzenes, benzene, toluene, xylenes, dichloroethane, chloroform, carbon tetrachloride and others. One particularly preferred solvent is o-xylene.

In addition to aniline or one of the other aromatic amines which are analogous to aniline for the purpose of the present invention, examples of which have been given above, the other starting material used in the process according to the present invention is formaldehyde, preferably in the form of an aqueous formalin solution.

At the beginning of the condensation reaction (at entry into reactor (3)), the molar ratio of aniline:formaldehyde is generally from 1:1 to 20:1, preferably from 2:1 to 8:1.

The volumetric ratio of (aniline + formaldehyde):water at the beginning of the condensation reaction (entry into reactor (3)) is generally from 2:1 to 1:10.

The degree of protonation at the beginning of the condensation reaction is generally from 30 to 100%, and preferably from 90 to 98%.

The degree of protonation of the aqueous phase carried to the main extraction stage (I) is generally from 40 to 70%, and preferably from 50 to 60%.

The hydrophobic solvent used in the main extraction stage (I) preferably has a free aniline content (or amine used instead of free aniline) of from 10 to 80%, by weight, and preferably from 40 to 60%, by weight.

The concentration of free amines in the aqueous phase and in the organic phase is preferably adjusted so that the solution pressure of free arylamine in the aqueous phase at the entry into extraction stage (I) is equal to or greater than the solution pressure of arylamine in the organic phase at the same point of the extraction stage.

The organic phase leaving extraction stage (I) is separated by distillation in conventional manner (distillation columns (8) or (8a) and (8b)) into solvent, aniline and the desired aniline/formaldehyde condensate. Separation of aniline from hydrophobic solvent is necessary only if a final washing with pure solvent is carried out in extractor (11) in order to obtain an increased degree of protonation in the aqueous phase. Separation of aniline and solvent in distillation stage (8) may generally be omitted since the aniline/solvent mixture may be used as such in the main extraction stage (I), if necessary after further addition of aniline.

The temperatures employed in the process according to the present invention are generally as follows: In a multistage condensation, the temperature in the first reactor is in the region of from 0° to 60° C, and preferably from 20° to 40° C, and in the last reactor is in the region of from 60° to 105° C, and preferably from 80° to 100° C.

Extraction in the main extraction stage (I) is generally carried out at temperatures of from 70° to 110° C, and preferably from 80° to 100° C.

The temperatures in the extractors of extraction stages (II) and (III) are generally from 20° to 110° C, and preferably from 35° to 100° C. It is advantageous in all the embodiments of the process according to the present invention if the efficiency of the extractors of extraction stage (III) is equal to or greater than the efficiency of the extractors of stage (II). The efficiency of the extractors is in particular a function of their construction (number of theoretical floors) and/or the temperature at which extraction is carried out.

The final washing in extractor (11) which may be carried out in embodiments 3 and 4 is generally carried out at a temperature of from 70° to 110° C, preferably from 80° to 100° C.

The structure of the apparatus used in the process according to the present invention, in particular of the condensation reactors, extractors and distillation columns, is of minor importance for carrying out the process according to the present invention. The conventional apparatus used in industrial chemistry for such reactions or separations may be employed.

It is immaterial to the process according to the present invention at what point the aniline is added to the whole system, preferably in the form of starting amine. The aniline need not necessarily be added at the beginning of the process or in the main extraction stage (I), as shown in the figures, but may also be added to the aqueous phase between the individual condensation reactions or at some other point between the exit from the last condensation reactor and the beginning of the process. If the process according to the present invention is carried out continuously, an equilibrium becomes established which is independent of the point at which aniline is added, but depends on and may be adjusted by, in particular, the quantity of aniline and formaldehyde fed into the system, the quantity of final product removed from the system, the rate of flow in the various solvent circulations and the temperature employed, particularly in the extractors.

The amine which is present at least in a partly protonated form in the aqueous phase returned to the beginning of the process does not, of course, consist exclusively of the amine used as starting material, which is preferably aniline, but may also include the 2,2'- and 2,4'-isomers mentioned above and N-(2-aminobenzyl)-aniline mentioned above, as well as other aniline/formaldehyde condensates, depending on the solution equilibria established during the individual extractions. These other amines, however, in no way impair the process according to the present invention since aniline reacts more rapidly with formaldehyde than aniline/formaldehyde condensates which have occupied parapositions although not more rapidly than the often unwanted ortho-isomers which have free parapositions.

In all the embodiments of the process according to the present invention, the water carried into the system, particularly with the aqueous formalin solution, and the water formed in the condensation reaction is preferably removed from the last reactor (4) by distillation.

The primary polyamines obtained by the process according to the present invention may be reacted with phosgene to form polyisocyanates by known methods. The process according to the present invention constitutes a substantial advance in the state of the art, in particular on account of its wide range of variation with regard to the distribution of isomers in the isolated product and particularly on account of the comparatively little effort required for distillation.

The process according to the present invention for the first time opens up the possibility in the production of aniline/formaldehyde condensates of isolating as a single product a substance which contains a lower proportion of 2,2'- and 2,4'-diaminodiphenylmethane than corresponds to the proportion of these isomers in the directly formed condensation product. This is due to the fact that 2,2'- and 2,4'-diaminodiphenylmethane formed in the condensation reaction are selectively extracted and continuously returned to the beginning of the process where they continue to react with a further quantity of formaldehyde to form higher nuclear condensates without being first worked-up and isolated.

In the process according to the present invention, other streams of solvent containing condensation product could be worked-up to isolate the product of the process instead of the stream of solvent leaving the main extraction stage (I) (extractor (5)). If, for example, it is desired to isolate an aniline/formaldehyde condensate containing a very high proportion of 2,2'- and 2,4'-diaminodiphenylmethane, this could be achieved by distillation of the stream of solvent leaving the extractor (7) of embodiment 3.

It should be recognized that although the term "one or more condensate stages" is and throughout the instant specification and claim, the reaction sequence occurs as follows (aniline and formaldehyde are shown for simplification):

The three reactions can occur in essentially one stage, such as shown in embodiments 1, 3, and 5, or they can occur in multiple stages as in embodiments 2, 4, 6 and 7.

Additionally, the term "containing aromatic amine" as used in the specification and claims is intended to mean that the particular stream can contain either a portion or the complete amount of final product. Thus, for example, the recycle solvent from the first extraction stage does contain portions of the final product.

In the Examples given below, the xylene used is in all cases o-xylene. The efficiency of the extractors of extraction stages (III) (extractors 7, 7a and 7b) is in all cases equal to or greater than the efficiency of the corresponding extraction stages (6, 6a and 6b) of the corresponding extraction stages (II).

EXAMPLE 1 (FIG. 1)

In a continuously operating experimental laboratory plant, a stream of substance (A) consisting of an aqueous hydrochloric acid solution of arylamine and a 30% aqueous formaldehyde solution (B) is continuously introduced into a cascade (reactors 3 and 4) consisting of six stirrer vessels. The two streams of substance have the following composition (in g/h):

Stream (A): 1200 aniline and
　　　　　190 polyamine mixture
　　　　　520 hydrogen chloride
　　　　　2300 water
Stream (B): 77 formaldehyde
　　　　　180 water.

As the reaction mixture flows through the cascade of tanks (reactors 3 and 4) its temperature rises from 35° C to its boiling point. In the last tank of reactor (4), the excess of water in the system (due to the water introduced in the form of formalin and the water produced in the condensation reaction) is reduced by distilling off at normal pressure a corresponding quanitity of water which is contaminated with methanol, xylene and aniline.

The reaction mixture leaving reactor (4) enters an extraction system consisting of three extraction columns (7), (5) and (6) through which the aqueous reaction solution flows successively in the order given.

In the first extraction column (7) an aniline-xylene mixture (8.5 kg/h, about 18%, by weight, of aniline) is passed in counterflow to the aqueous stream.

The aqueous phase enriched with aniline then enters extractor (5) in which the reaction product is extracted at from 90° to 95° C by means of a mixture of aniline and xylene in the proportions, by weight of 1.1:1.0 of the components. The proportion by weight of the substance used for extraction to the extracted phase is about 2:1.

The extract phase leaving extraction column (5) is freed from traces of acid carried along with it by a process of washing with water and dilute sodium hydroxide solution (not represented in FIG. 1). In distillation apparatus (8), a mixture of aniline and xylene is distilled off and the condensation product is obtained as distillation sump and collected in the product receiver (10).

The distillate from (8) is adjusted to the required composition of aniline:xylene of 1.1:1.0 by the addition of fresh aniline from container (1) and again used for extraction in (5).

The phase leaving (5), which has now become depleted of product, enters a third extraction column (6) in which aniline is removed from it by a multistage extraction process at from 90° to 95° C by means of the xylene phase from extractor (7), which has become depleted of aniline (aniline content from about 2 to 3%), this extraction process being continued until the aqueous phase leaving (6) has approximately the composition of stream (A), and this aqueous phase is then returned to the beginning of the process. Before it is again reacted with formaldehyde in reactor (3), the exact ratio of amine to HCl required for the reaction is adjusted by the addition of small quantites of aniline from container (1).

The organic phase leaving extractor column (6), which is enriched with aniline, is returned to extractor (7) and used for the process.

The product obtained (about 500 g/h) from the embodiment of the process according to the present invention exemplified above contains on average from 85 to 88% of diaminodiphenylmethane, 96.5% of which consist of the 4,4'-isomer.

EXAMPLE 2 (FIG. 2)

In a continuously operated experimental laboratory plant, the stream of substance (A) consisting of an aqueous hydrochloric acid solution of arylamine and a stream of substance (B) consisting of an aqueous formalin solution are continuously introduced into the reactor (3) which consists of three tanks equipped with stirrers. The temperature in reactor (3) is maintained at from 35° to 40° C. The two streams of substance have the following composition (in g/h):

Stream (A): 1200 aniline and
 190 polyamine mixture
 520 hydrogen chloride
 2300 water
Stream (B): 77 formaldehyde
 180 water.

The aqueous reaction mixture from reactor (3) enters extraction column (7) in which it flows in countercurrent to an aniline/xylene mixture (8.5 kg/h, about 18%, by weight, of aniline) which is obtained in extractor (6) and from which it absorbs most of the aniline (about 1.4 kg/h) in the course of a multistage extraction process.

The aqueous phase leaving extractor (7) and now enriched with aniline is heated to the boiling point of the mixture to complete the reaction in reactor (4) which also consists of three tanks equipped with stirrers. In the last tank of reactor (4), the excess of water in the system (due to the water introduced in the form of formalin and the water produced by the condensation reaction) is removed from the system by distilling off at normal pressure a corresponding quantity of water which is contaminated with methanol, xylene and aniline. The reaction mixture then flows from reactor (4) into extractor (5).

The subsequent stages of the process are analogous to those described in Example 1. The product obtained (about 500 g/h) from the embodiment of the process according to the present invention described in Example 2 contains on average from 92 to 95% of diaminodiphenylmethanes, from 94.5 to 95.5% of which consist of the 4,4'-isomer.

EXAMPLE 3 (FIG. 3)

In a continuously operating experimental laboratory plant, a stream of substance (A) consisting of an aqueous hydrochloric acid solution of arylamine and a stream of substance (B) consisting of a 30% aqueous formalin solution are continuously introduced into a cascade (reactors 3 and 4) consisting of six tanks equipped with stirrers. The two streams of substance have the following composition (g/h):

Stream (A): 1150 aniline and
 250 polyamine mixture
 520 hydrogen chloride
 2300 water
Stream (B): 77 formaldehyde
 180 water.

As the reaction mixture passes through the cascade of tanks (reactor 3 and 4), its temperature rises from 35° C to its boiling point. In the last tank of the reactor (4), the excess of water produced in the system by the water introduced in the form of formalin and the water formed in the condensation reaction is reduced by distilling off at normal pressure a corresponding quantity of water contaminated with methanol, xylene and aniline.

400 g/h of aniline (not shown) are added to the reaction mixture leaving the reactor (4) before it enters an extraction system consisting of four extraction columns (7), (5), (6) and (11) through which the aqueous reaction solution flows successively in that order.

In the first extraction column (7), an aniline/xylene mixture (volumetric ratio of organic phase to aqueous phase approximately 2:1) which has an amine content of from about 25 to 30%, by weight, is passed in countercurrent to the aqueous substance stream.

The aqueous phase enriched with aniline then enters extractor (5) in which from 90 to 95% of the reaction product is replaced by aniline and extracted by means of an aniline/xylene mixture containing aniline and xylene in proportions, by weight, of 1.1:1.0. The proportions by weight of the substance used for extraction to the extracted phase is from about 1.5:1 to 2:1.

The extract phase leaving extraction column (5) is freed from traces of acid carried along with it by a process of washing (not shown in FIG. 3) with water and dilute sodium hydroxide solution. The extract is then separated into xylene, aniline and condensation product (distillation sump) in the two-stage distillation apparatus (8a) and (8b). While xylene is returned directly into the extraction cycle, the product is collected in container (10) while the aniline together with aniline freshly added to the system is distributed to the various inlet points of the installation by way of container (1).

The aqueous phase leaving (5) depleted of product enters a third extraction column (6) in which the organic phase from extractor (7), which is depleted of aniline (amine content from about 15 to 20%) extracts aniline from it in a multistage extraction process at from 90° to 95° C until the equilibrium state is reached (about 1 kg/h). Aniline remaining in the aqueous phase is then extracted with pure xylene in the following extractor (11) until the aqueous phase has a degree of protonation and approximate composition of the substance stream (A) in the discharged aqueous phase which is returned to the beginning of the process. Before it is again reacted with formaldehyde in reactor (3), the exact ratio of amine to catalyst required for the reaction is adjusted by the addition of small quantities of aniline from container (1) so that the composition of substance stream (A) indicated above is again obtained.

The organic phase leaving extraction column (6), which is now enriched with aniline, is returned to extractor (7) and used.

The product obtained (about 500 g/h) in the embodiment of the process according to the present invention exemplified above has an average diaminodiphenylmethane content of from 84 to 85%, of which from 98 to 99% consists of the 4,4'-isomer.

EXAMPLE 4 (FIG. 4)

In a continuously operated experimental laboratory plant, a stream of substance (A) consisting of an aqueous hydrochloric acid solution of arylamine and a stream of substance (B) consisting of a 30% aqueous formalin solution are continuously introduced into reactor (3) which consists of three tanks equipped with stirrers, the temperature in reactor (3) being maintained at from 35° to 40° C. The two streams of substance have the following composition (in g/h):

Stream (A): 1050 aniline and
 350 polyamine mixture
 517 hydrogen chloride
 2290 water Stream (B): 77 formaldehyde
          180 water.

400 g/h of aniline are added (not shown) to the reaction mixture leaving reactor (3) before it enters an extraction column (7) where it is carried in countercurrent to the aniline/xylene mixture from extractor (6) (ratio by volume of organic phase to aqueous phase approximately 2:1) in which the amine content falls to from about 15 to 20%, by weight, due to transfer of aniline to the aqueous phase (about 1 kg/h) in the course of the multistage extraction process. From 3 to 4%, by weight, thereof consists of condensation products.

The aqueous phase leaving extractor (7), which is now enriched with aniline, is heated to the boiling point of the mixture in reactor (4) (also consisting of three tanks equipped with stirrer) to complete the reaction. In the last tank of reactor (4), the excess of water present in the system due to the water introduced in the form of formalin and the water formed by the condensation reaction is removed by distilling off at normal pressure a corresponding quantity of water which is contaminated with methanol, xylene and aniline. The reaction mixture leaving reactor (4) then enters extractor (5).

The subsequent stages of the process are analogous to those described in Example 3. The product obtained (about 500 g/h) in the embodiment of the process according to the present invention described in Example 4 contains on average from 92 to 95% of diaminodiphenylmethanes, from 94 to 96% of which are in the form of the 4,4'-isomer.

EXAMPLE 5 (FIG. 5)

In a continuously operated experimental laboratory plant, a stream of substance (A) consisting of an aqueous hydrochloric acid solution of arylamine and a stream of substance (B) consisting of a 30% aqueous formalin solution are continuously introduced into a cascade (reactors 3 and 4) of six tanks equipped with stirrers. The two streams of substance have the following composition (in g/h)

Stream (A): 1165 aniline and
          250 polyamine mixture
          517 hydrogen chloride
          2290 water
Stream (B): 77 formaldehyde
          180 water.

As the reaction mixture flows through the cascade of tanks (reactors 3 and 4), its temperature rises from 35° C to its boiling point. In the last tank of reactor (4) the excess of water present in the system due to the water introduced in the form of formalin and the water produced by the condensation reaction is removed by distilling off at normal pressure a corresponding quantity of water contaminated with methanol, xylene and aniline.

The reaction mixture leaving reactor (4) enters an extraction system consisting of five extraction columns (7a), (7b), (5), (6b) and (6a) through which the aqueous reaction solution flows in that order.

In the first extraction column (7a), a mixture of aniline and xylene (8.5 kg/h, approximately 18%, by weight, of aniline) from (6a) is carried in countercurrent to the aqueous stream from (4). The aniline in this organic phase is practically completely taken up by the aqueous phase in the course of a multistage extraction process so that the degree of protonation (ratio of amine equivalents to HCl equivalents) therein falls to from about 70 to 80%. The xylene now depleted of aniline (from about 2 to 3% of aniline) is used again in (6a).

The aqueous phase from (7a) enters the second extraction column (7b) where it takes up a further quantity of aniline from a mixture of aniline and xylene (ratio by volume of organic phase to aqueous phase about 2:1, amine content of organic phase from about 25 to 30%, by weight) introduced from (6b). Since the aniline content in the aqueous phase was already increased in (7a), the organic phase leaving the multistage extraction process at (7b) contains from about 15 to 20% of amine and from about 1 to 2% of reaction products, including the small quantitites of intermediate products (aminobenzyl anilines) still present at this point. The end products obtained here (diaminodiphenylmethane) contain a much higher proportion of ortho-isomers (2,2'- and 2,4'-diaminodiphenylmethane) than is produced in the reaction.

The aqueous phase which has been enriched with aniline in (7a) and (7b) enters extraction column (5). Extraction in (5) and treatment and working-up of the extract obtained from (5) are carried out as described in Examples 1 and 2.

The aqueous phase leaving (5), which is depleted of product, now enters a fourth extraction column (6b) in which a part of the aniline is removed from it by a multistage extraction process at from 90° to 95° C by the mixture of aniline and xylene obtained from (7b), this removal of aniline continuing until equilibrium has been established. At the same time, the condensation products in the organic phase move in the reverse direction into the aqueous phase until equilibrium is established.

In another, fifth extraction column (6a), the xylene phase from (7a), which is depleted of aniline, extracts aniline from the aqueous phase in a multistage extraction at from 90° to 95° C until the aqueous phase leaving (6a) has approximately the composition of the stream of substance (A) at which point it is returned to the beginning of the process while the organic phase enriched with aniline is used again at (7a).

The product obtained (about 500 g/h) in this embodiment of the process exemplified above contains on average from 84 to 85% of diaminodiphenylmethanes, from about 98 to 99% of which consist of the 4,4'-isomer.

EXAMPLE 6 (FIG. 6)

In a continuously operated experimental laboratory plant, a stream of substance (A) consisting of an aqueous hydrochloric acid solution of arylamine and a stream of substance (B) consisting of a 30% aqueous formalin solution are continuously introduced into the reactor (3) consisting of three tanks equipped with stirrers, the temperature in reactor (3) being maintained at from 35° to 40° C. The two streams of substance have the following composition (g/h):

Stream (A): 1165 aniline and
          250 polyamine mixture
          517 hydrogen chloride
          2290 water
Stream (B): 77 formaldehyde
          180 water.

The aqueous reaction mixture leaves reactor (3) to enter a first extraction column (7a) in which a mixture of aniline/xylene (8.5 kg/h, about 18%, by weight, of aniline) from (6a) is carried in countercurrent to it. In the course of a multistage extraction process, the aniline in the organic phase is practically completely taken up by the aqueous phase, the degree of protonation (ratio of amine equivalent to HCl equivalent) therein being thereby reduced to from about 70 to 80%. The xylene now depleted of aniline (about 1% aniline) is used again in (6a).

The aqueous phase leaving extractor (7a) enriched with aniline is then heated to boiling to complete the reaction in reactor (4) which also consists of three tanks equipped with stirrers. In the last tank of reactor (4), the excess of water present in the system due to the water introduced in the form of formalin and the water produced in the condensation reaction is reduced by distilling off at normal pressure a corresponding quantity of water which is contaminated with methanol, xylene and aniline.

The reaction mixture leaving reactor (4) enters extraction column (7b) and from then on the procedure is analogous to that described in Example 5.

The product obtained (about 500 g/h) in the embodiment of the process described in Example 6 contains on average from 89 to 92% of diaminodiphenylmethanes, from about 97 to 99% of which consists of the 4,4'-isomer.

EXAMPLE 7 (FIG. 7)

In a continuously operated experimental laboratory plant, a stream of substance (A) consisting of an aqueous hydrochloric acid solution of arylamine and a stream of substance (B) consisting of a 30% aqueous formalin solution are continuously introduced into a reactor (3) consisting of three tanks equipped with stirrers, the temperature in reactor (3) being maintained at from 35° to 40° C. The two streams of substance have the following composition (in g/h):

Stream (A): 1060 aniline and
340 polyamine mixture
517 hydrogen chloride
2290 water Stream (B): 77 formaldehyde
180 water.

The aqueous reaction mixture leaving reaction (3) enters a first extraction column (7a) in which aniline/xylene mixture (8.5 kg/h, about 18%, by weight, of aniline) from (6a) is carried in countercurrent to it. In the course of a multistage extraction process, the aniline in the organic phase is practically completely taken up by the aqueous phase, in which the degree of protonation (ratio of amine equivalents to HCl equivalents) is thereby reduced to from about 70 to 80%. The xylene now depleted of aniline (from about 2 to 3% of aniline) is used again in (6a).

The aqueous phase from (7a) enters a second extraction column (7b) where it takes up a further quantity of aniline from an aniline/xylene mixture supplied from (6b). Since in (7a) the aniline content of the aqueous phase was already raised above that of the starting solution, the organic phase leaving (7b) at the end of the multistage extraction process contains about 15% of amines when equilibrium has been established, from about 20 to 30% of which consist of condensation products, mainly aminobenzylanilines, which move in the opposite direction from the aqueous condensation solution into the organic phase, again due to establishment of equilibrium. Here again, enrichment of the organic phase with ortho-isomers is observed.

The aqueous phase which has become enriched with aniline in (7a) and (7b) is heated to the boiling point of the mixture in reactor (4) (also consisting of three tanks with stirrers) to complete the reaction. In the last tank of reactor (4), the excess of water present in the system due to the water introduced in the form of formalin and the water formed in the condensation reaction is removed by distilling off at normal pressure a corresponding quantity of water contaminated with methanol, xylene and aniline.

The completely aqueous phase leaving reactor (4) enters extraction column (5). Extraction in (5), treatment and working-up of the extract from (5), and stages (6a) and (6b) of the process are carried out in a manner analogous to that described in Examples 5 and 6.

The product obtained in the embodiment of the process exemplified about (about 500 g/h) has an average diaminodiphenylmethane content of from 92 to 95%, more than from 94 to 96% of which consists of the 4,4'-isomer.

It is to be understood that any of the components and conditions mentioned as suitable herein can be sutstituted for its counterpart in the foregoing examples and that although the invention has been described in considerable detail in the foregoing, such detail is solely for the purpose of illustration. Variations can be made in the invention by those skilled in the art without departing from the spirit and scope of the invention except as it may be limited by the claims.

What is claimed is:

1. In a process for the preparation of multinuclear aromatic polyamines by the condensation of aniline with formaldehyde in the presence of water and acid catalysts, in which the completely reacted aqueous condensation mixture is extracted with a hydrophobic solvent in extraction stage (I), optionally with the addition of aniline, the resulting solvent phase is worked-up in known manner to isolate the polyamine and the aqueous phase is recycled to the beginning of the process, the improvement characterised in that before the aqueous phase is returned to the beginning of the process, it is extracted in one or more separate extractors (II) with a hydrophobic solvent which may contain aniline and/or aniline/formaldehyde condensates with an increased proportion of ortho-isomers, the resulting solvent phase or phases is or are extracted with the aqueous acid condensation mixture in one or more separate extractors (III) at any one or more points after the first condensation stage and before the main extraction stage (I), and the resulting solvent phase or phases is or are returned to extractor or extractors (II).

2. In a process for the preparation of multinuclear aromatic polyamines having a reduced 2,2'- and 2,4'-diaminodiphenylmethane content by the condensation of aniline and formaldehyde in the presence of water and acid catalysts, the improvement characterised in that 2,2'- and 2,4'-diaminodiphenylmethane are selectively extracted from the reaction mixture formed in the condensation reaction and the extracted 2,2'- and 2,4'-diaminodiphenylmethane are returned to the beginning of the process, and the reaction mixture depleted of the aforesaid isomers by this selective extraction is worked-up to obtain polyamines of the diphenylmethane series.

3. A process for the preparation of multinuclear aromatic polyamines which comprises of steps:

(A) condensing an aromatic amine with formaldehyde in the presence of an aqueous acid catalyst to obtain the condensation mixture as a first aqueous phase containing said aromatic polyamines, (B) extracting a first solvent phase with said first aqueous phase to provide a second solvent phase and a second aqueous phase containing said aromatic polyamines, (C) extracting said second aqueous phase with a hydrophobic solvent to provide a third solvent phase and a third aqueous phase containing the acid catalyst as an amine salt of said aromatic amine and of said aromatic polyamine, (D) recovering said aromatic polyamines from said third solvent phase, (E) extracting said third aqueous phase with said second solvent phase to provide said first solvent phase and a fourth aqueous phase containing the acid catalyst and amine salt of said aromatic amines and of said aromatic polyamines, (F) returning said first solvent phase to step (B), and (G) returning said fourth aqueous phase to step (A).

4. The process of claim 3, wherein step (E) comprises two or more extraction stages.

5. The process of claim 4, wherein said step (E) comprises:

(Ei) extracting said third aqueous phase with said second solvent phase to provide said first solvent phase, and a fifth aqueous phase containing the acid catalyst as an amine salt of said aromatic amine and of said aromatic polyamines, and (Eii) extracting said fifth aqueous phase with a hydrophobic solvent to provide a fourth solvent phase and said fourth aqueous phase containing the acid catalyst as an amine salt of said aromatic amine and of said aromatic polyamines.

6. The process of claim 5, wherein said fourth solvent phase is returned to step (C).

7. The process of claim 3, wherein both steps (B), and steps (E), comprises two or more extraction stages.

8. The process of claim 7, wherein step (B) comprises:

(Bi) extracting said first solvent phase with said first aqueous phase to provide said second solvent phase and a sixth aqueous phase containing said aromatic polyamines, and (Bii) extracting a fourth solvent phase with said sixth aqueous phase to provide a fifth solvent phase and said second aqueous phase containing said aromatic polyamines, and wherein step (E) comprises:

(Ei) extracting said third aqueous phase with said fifth solvent phase to provide said fourth solvent phase and a seventh aqueous phase containing the acid catalyst as an amine salt of said aromatic amine and of said aromatic polyamines, (Eii) returning said fourth solvent phase to step (Bii), and (Eiii) extracting said seventh aqueous phase with said second solvent phase to provide said first solvent phase and said fourth aqueous phase containing the acid catalyst as an amine salt of said aromatic amine and of said aromatic polyamines.

9. A process for the preparation of multi-nuclear aromatic polyamines which comprises the steps:

(A) pre-condensing an aromatic amine with formaldehyde in the presence of an aqueous acid catalyst in a first condensation stage to obtain a precondensation mixture as a first aqueous phase, (B) extracting a first solvent phase with said first aqueous phase to provide a second solvent phase and a second aqueous phase, (C) subjecting said second aqueous phase to a final condensation reaction to obtain a condensation mixture as a third aqueous phase containing said aromatic polyamines, (D) extracting said third aqueous phase with a hydrophobic solvent to provide a third solvent phase and a fourth aqueous phase containing the acid catalyst as an amine salt of said aromatic amine and of said aromatic polyamines, (E) recovering said aromatic polyamines from said third solvent phase, (F) extracting said fourth aqueous phase with said second solvent phase to provide said first solvent phase and a fifth aqueous phase containing the acid catalyst as amine salt of said aromatic amine and of said aromatic polyamines, (G) returning said first solvent phase to step (B), and (H) returning said fifth aqueous phase to step (A).

10. The process of claim 9, wherein said step (F) comprises two or more extraction stages.

11. The process of claim 10, wherein said step (F) comprises:

(Fi) extracting said fourth aqueous phase with said second solvent phase to provide said first solvent phase and a sixth aqueous phase containing the acid catalyst as an amine salt of said aromatic amine and of said aromatic polyamines, and (Fii) extracting the sixth aqueous phase with a hydrophobic solvent to provide a fourth solvent phase and said fifth aqueous phase containing the acid catalyst as amine salt of said aromatic amine and of said aromatic polyamines.

12. The process of claim 11, wherein said fourth solvent phase is returned to step (D).

13. The process of claim 9, wherein steps (B) and (F) comprise two or more extraction stages.

14. The process of claim 13, wherein step (B) comprises:

(Bi) extracting said first solvent phase with said first aqueous phase to provide said second solvent phase and a seventh aqueous phase and, (Bii) extracting a fourth solvent phase with said seventh aqueous phase to provide a fifth solvent phase and said second aqueous and, wherein step (F) comprises:

(Fi) extracting said fourth aqueous phase with said fifth solvent phase to provide said fourth solvent phase and a eighth aqueous phase containing the acid catalyst as an amine salt of said aromatic amine and of said aromatic polyamines, (Fii) returning said fourth solvent phase to step (Bii), and (Fiii) extracting said eighth aqueous phase with said second solvent phase to provide said first solvent phase and said fifth aqueous phase containing the acid catalyst as an amine salt of said aromatic amine and of said aromatic polyamines.

15. A process for the preparation of multi-nuclear aromatic polyamines comprising the steps:

(A) precondensing an aromatic amine with formaldehyde in the presence of an aqueous acid catalyst in a first condensation stage to obtain a precondensation mixture as a first aqueous phase, (B) extracting a first solvent phase with said first aqueous phase to provide a second solvent phase and a second aqueous phase, (C) subjecting said second aqueous phase to a final condensation reaction to obtain a condensation mixture as a third aqueous phase containing said aromatic polyamines, (D) extracting a third solvent phase with said third aqueous phase to provide a fourth solvent phase and a fourth aqueous phase containing aromatic polyamines, (E) extracting said fourth aqueous with a hydrophobic solvent to provide a fifth solvent phase and a fifth aqueous phase containing the acid catalyst as an amine salt of said aromatic amine and of said aromatic polyamines, (F) recovering said aromatic polyamines from said fifth solvent phase, (G) extracting said fifth aqueous phase with said fourth solvent phase to provide said third solvent phase and a sixth aqueous phase containing the acid catalyst as an amine salt of said aromatic amine and of said aromatic polyamines, (H) returning said third solvent phase to step (D), (I) extracting said sixth aqueous phase with said second solvent phase to provide said first solvent phase and a seventh aqueous phase containing the acid catalyst as an amine salt of said aromatic amine and of said aromatic polyamines, (J) returning said first solvent phase to step (B), and (K) returning said seventh aqueous phase to step (A).

* * * * *